(12) United States Patent
Perkins et al.

(10) Patent No.: US 9,891,163 B2
(45) Date of Patent: Feb. 13, 2018

(54) INCORPORATION OF INTEGRATED COMPUTATIONAL ELEMENTS WITHIN OPTICAL ANALYSIS TOOLS HAVING A MINIATURIZED OPERATIONAL PROFILE

(71) Applicant: Halliburton Energy Services, Inc., Houston, TX (US)

(72) Inventors: David L. Perkins, The Woodlands, TX (US); Darren G. Gascooke, Houston, TX (US); Nagaraja Pai, Houston, TX (US); Nathan J. Harder, Powell, WY (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 15/316,878

(22) PCT Filed: Nov. 10, 2015

(86) PCT No.: PCT/US2015/059820
§ 371 (c)(1),
(2) Date: Dec. 7, 2016

(87) PCT Pub. No.: WO2017/082864
PCT Pub. Date: May 18, 2017

(65) Prior Publication Data
US 2017/0284931 A1 Oct. 5, 2017

(51) Int. Cl.
*G01N 21/31* (2006.01)
(52) U.S. Cl.
CPC ..... *G01N 21/31* (2013.01); *G01N 2201/0633* (2013.01)

(58) Field of Classification Search
CPC ........ G01N 21/31; G01N 21/3586; G01J 3/28
USPC .................................. 250/214.1, 214 R, 221
See application file for complete search history.

(56) References Cited

U.S. PATENT DOCUMENTS

| | | | |
|---|---|---|---|
| 6,040,578 A * | 3/2000 | Malin | A61B 5/14532 250/339.11 |
| 8,895,928 B2 | 11/2014 | Pai et al. | |
| 2003/0092208 A1 | 5/2003 | Trezza et al. | |
| 2009/0219597 A1 | 9/2009 | Myrick et al. | |
| 2013/0286399 A1 | 10/2013 | Freese et al. | |

(Continued)

OTHER PUBLICATIONS

ISR/WO for PCT/US2015/059820 dated Aug. 10, 2016.

*Primary Examiner* — Que T Le
(74) *Attorney, Agent, or Firm* — McDermott Will & Emery LLP

(57) ABSTRACT

Conventional optical analysis tools containing an integrated computational element may have an operational profile that is too large for convenient use within confined locales. Optical analysis tools having a miniaturized operational profile can comprise: an electromagnetic radiation source that provides electromagnetic radiation to an optical train; and an optical computing device positioned within the optical train. The optical computing device comprises a planar array detector having at least two optical detection regions. At least one of the at least two optical detection regions has an integrated computational element disposed thereon. The planar array detector and the integrated computational element are in a fixed configuration with respect to one another.

22 Claims, 5 Drawing Sheets

(56) References Cited

U.S. PATENT DOCUMENTS

2014/0172177 A1 6/2014 Jamison et al.
2015/0212232 A1 7/2015 Perkins et al.

* cited by examiner

INCORPORATION OF INTEGRATED COMPUTATIONAL ELEMENTS WITHIN OPTICAL ANALYSIS TOOLS HAVING A MINIATURIZED OPERATIONAL PROFILE

BACKGROUND

The present disclosure generally relates to optical computing, and, more specifically, to optical analysis tools having an operational profile that is smaller than that conventionally attainable.

Spectroscopic analyses are well known for their versatility for detecting a wide variety of substances. Most spectroscopic instruments are general purpose and are not configured to detect any one particular substance or class of substance. Accordingly, involved and time-consuming spectral processing and/or sample preparation operations may be needed to analyze for a particular substance within a given sample. Although spectroscopic analyses can often be routinely carried out under regulated laboratory conditions, they can be considerably more difficult to transition into less controlled environments, such as the oilfield and other process settings, where operational conditions may damage and/or limit the accuracy of conventional spectroscopic equipment and techniques.

Optical computing devices represent an alternative to conventional spectroscopic equipment and techniques. As used herein, the term "optical computing device" will refer to an optical device configured to receive an input of electromagnetic radiation from a sample and produce an output of electromagnetic radiation from a processing element that is diagnostic of a characteristic of the sample. Optical computing devices utilize an integrated computational element (ICE), also referred to as an "ICE core," which is a processing element that is specifically designed to analyze for a given component or characteristic of interest in a sample upon optical interaction of electromagnetic radiation therewith. As used herein, the term "integrated computational element" will refer to an optical processing element containing a plurality of optical thin film layers formed from various materials whose indices of refraction and thicknesses may vary between each layer. The layer compositions, thicknesses, and ordering may be chosen, based upon calculations, to selectively transmit or reflect predetermined fractions of electromagnetic radiation at different wavelengths such that the integrated computational element is configured to substantially mimic the regression vector corresponding to a particular component or characteristic of interest in a sample.

As used herein, the term "characteristic" will refer to a substance's concentration in a sample or a derived physical property for the sample. The transmission or reflection function of the integrated computational element may represent the regression vector for a characteristic of interest, and the transmission or reflection function may be weighted with respect to wavelength. Accordingly, upon optically interacting electromagnetic radiation with a sample and with an integrated computational element, the electromagnetic radiation may change in a known and specific way that may be representative of the characteristic's magnitude in the sample. Following receipt of the electromagnetic radiation by a detector, an output from the detector can be correlated to the characteristic of interest, optionally after additional computational processing takes place. Even though a complex mixture of substances may be present in a given sample, the integrated computational element may be able to distinguish and analyze for a particular substance or characteristic based on the unique regression vector represented by the integrated computational element.

Optical computing devices may be advantageous compared to conventional spectroscopic techniques, since optical computing analyses may be conducted rapidly, often in real-time, with limited to no sample preparation involved. Rather than obtaining an optical spectrum as in conventional spectroscopic techniques, which may require further interpretation and deconvolution to take place, the output of optical computing devices is a real number that is correlatable to a characteristic of interest. Optical computing devices are also much more rugged than conventional spectroscopic equipment and can be deployed in locales where spectroscopic analyses may otherwise be problematic. Accordingly, optical computing devices may often be desirable for analyzing complex mixtures in various process environments, such as those encountered in the oilfield industry.

Optical computing analyses may utilize a single integrated computational element or, more commonly, a plurality of integrated computational elements. A plurality of integrated computational elements may be used to analyze for multiple characteristics of a sample or a single sample characteristic. Using multiple integrated computational elements to analyze for a single sample characteristic may involve optically interacting electromagnetic radiation with the sample and with multiple integrated computational elements in sequence or by computationally combining the outputs of two or more integrated computational elements with one another. Benefits that may be realized when utilizing multiple integrated computational elements in the analysis of a single characteristic of interest include, but are not limited to, increased analytical sensitivity, signal normalization and combinations thereof.

Conventional optical computing device configurations containing multiple integrated computational elements include, for example, disposing the integrated computational elements along an extended optical train or housing the integrated computational elements on a movable assembly that allows different integrated computational elements to be exposed to electromagnetic radiation at various points in time (e.g., through lateral or rotational motion of the movable assembly). Either device configuration, however, can result in an operational profile that is too bulky to fit effectively within confined locales. In addition to the space occupied by a movable assembly itself, the operating mechanisms needed to produce lateral or rotational motion can sometimes exceed the available space in confined locales, such the space within or in proximity to a tubular string within a subterranean wellbore. Furthermore, extreme downhole operating conditions can also be taxing to such operating mechanisms and the necessity to supply power downhole thereto can be problematic in many aspects.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, as will occur to one having ordinary skill in the art and the benefit of this disclosure.

DETAILED DESCRIPTION

The present disclosure generally relates to optical computing, and, more specifically, to optical analysis tools having an operational profile that is smaller than that conventionally attainable.

One or more illustrative embodiments incorporating the features of the present disclosure are presented herein. Not all features of a physical implementation are necessarily described or shown in this application for the sake of clarity. It is to be understood that in the development of a physical implementation incorporating the embodiments of the present disclosure, numerous implementation-specific decisions may be made to achieve the developer's goals, such as compliance with system-related, business-related, government-related and other constraints, which may vary by implementation and from time to time. While a developer's efforts might be time-consuming, such efforts would be, nevertheless, a routine undertaking for one having ordinary skill in the art and the benefit of this disclosure.

As discussed above, optical computing devices containing an integrated computational element may provide a number of advantages over conventional spectroscopic techniques, not to mention wet chemical analyses. In this regard, integrated computational elements may be specifically designed to analyze for a particular characteristic of interest, even in samples containing a complex mixture of substances. A plurality of integrated computational elements may be used to conduct analyses for a single characteristic or multiple characteristics. However, conventional optical computing devices containing a plurality of integrated computational elements sometimes possess an operational profile that may exceed the available operating space in confined locales.

Figure 1:
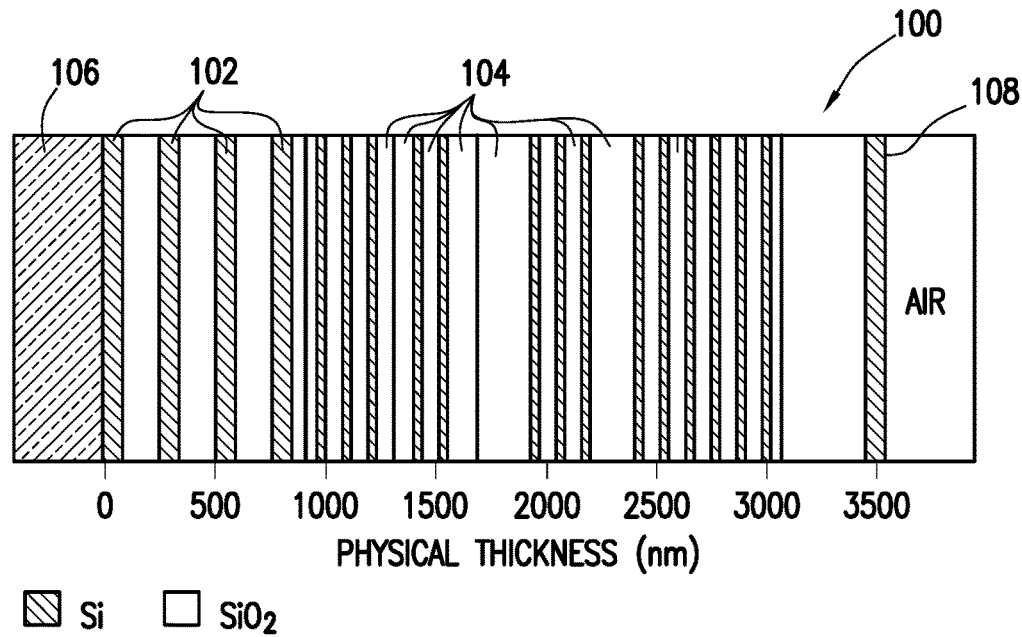
FIG. 1 is a diagram that illustrates an exemplary integrated computational element (ICE).

Before further discussing how the operational profile of optical computing devices may be miniaturized, according to the embodiments of the present disclosure, a brief discussion of illustrative integrated computational elements and optical computing devices is provided hereinafter. FIG. 1 is a diagram that illustrates an exemplary integrated computational element (ICE) 100. As illustrated, ICE 100 may include a plurality of alternating layers 102 and 104, such as silicon (Si) and $SiO_2$ (quartz), respectively. In general, layers 102 and 104 consist of materials whose index of refraction is high and low, respectively. Other examples may include niobia and niobium, germanium and germania, $MgF$, $SiO_x$, and other high and low index materials known in the art.

Layers 102 and 104 may be strategically deposited on optical substrate 106. As used herein, the term "optical substrate" will refer to a surface upon which layers 102 and 104 of an integrated computational element are deposited and which does not substantially optically interact with electromagnetic radiation over a wavelength range where the regression vector is being mimicked. That is, optical substrate 106 provides mechanical support for layers 102 and 104 and exhibits a substantially flat or known optical profile, such as an optical transmission profile, in the wavelength range over which ICE 100 is operational. In some embodiments, optical substrate 106 may be BK-7 optical glass. In other embodiments, optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like. Although some of the materials that may comprise optical substrate 106 are among those that may comprise layers 102 and 104, the layer thicknesses when used as optical substrate 106 are often much thicker. Opposite optical substrate 106, ICE 100 may include layer 108 that is generally exposed to the environment of the device or the sample undergoing analysis. Layer 108 may comprise the same material or a different material than optical substrate 106.

It should be understood that exemplary ICE 100 is not intended to be predictive for any particular characteristic of interest, but is provided for purposes of illustration only. Consequently, when analyzing for a particular characteristic of interest, the number of layers 102 and 104, their composition and their thicknesses may vary. Moreover, the materials that make up each layer 102 and 104 (i.e., Si and $SiO_2$) may vary, depending on the application, cost of materials, and/or applicability of the materials to the monitored characteristic.

The number, thickness and composition, for example, of layers 102 and 104 may be determined by performing a conventional spectroscopic analysis and then mimicking the regression vector for determining a characteristic of interest by iteratively processing the various layer parameters to best reproduce or "best fit" the regression vector. A number of mathematical solutions may be obtained in this regard, and the various mathematical solutions may then be fabricated and further tested to determine if the ICE can provide a quality analysis of the characteristic of interest in practice. The regression vector being mimicked with ICE 100 typically includes any number of different wavelengths and may encompass one or more regions of the electromagnetic spectrum.

In some embodiments, the material of each layer 102 and 104 may be doped or two or more materials may be combined in a manner to achieve the desired optical performance. In addition to solids, exemplary ICE 100 may also contain liquids and/or gases, optionally in combination with solids, in order to produce a desired optical performance. In the case of gases and liquids, ICE 100 may contain a corresponding vessel (not shown), which houses the gases or liquids. Exemplary variations of ICE 100 may also include holographic optical elements, gratings, piezoelectrics, light pipe, digital light pipe (DLP), molecular factor devices, variable optical attenuators, frequency selective surface (FSS) elements, and/or acousto-optic elements, for example, that can create transmission, reflection, and/or absorptive properties of a material of interest.

The multiple layers 102 and 104 exhibit different refractive indices. By properly selecting the materials of layers 102 and 104, their relative thicknesses and spacing, ICE 100 may be configured to selectively transmit, reflect, or refract predetermined fractions of electromagnetic radiation at different wavelengths. Each wavelength is given a predetermined weighting or loading factor. The thickness and spacing of layers 102 and 104 may be determined using a variety of approximation methods from a spectrum of a substance of interest. These methods may include inverse Fourier transform (IFT) of the optical transmission spectrum and structuring ICE 100 as the physical representation of the IFT. The approximations convert the IFT into a structure based on known materials with constant refractive indices.

The weightings that layers 102 and 104 of ICE 100 apply at each wavelength are set to the regression weightings described with respect to a known equation, data, or spectral signature. Briefly, ICE 100 may be configured to perform the dot product of the input electromagnetic radiation into ICE 100 and a desired loaded regression vector represented by each layer 102 and 104 for each wavelength. As a result, the output intensity of the electromagnetic radiation from ICE 100 is related to the characteristic of interest.

A plurality of integrated computational elements may be present in a single optical computing device. The plurality of integrated computational elements may be used to analyze for multiple characteristics, or the output from multiple integrated computational elements may be combined (e.g., physically and/or computationally) to analyze for a single characteristic. Although integrated computational elements are by themselves relatively small, optical computing device configurations containing a plurality of integrated computational elements can exceed the available space in confined analysis locales.

The present inventors discovered alternative configurations for deploying integrated computational elements within optical computing devices. These configurations can facilitate miniaturization of the operational profile of optical computing devices and can be particularly beneficial when placing multiple integrated computational elements within a limited amount of space. In addition, the inventors made further parallel discoveries that are usable in combination with either conventional optical computing device configurations or the configurations disclosed herein to allow further decreases in operational profile to be realized. These additional advances are also discussed in detail hereinbelow.

Concerning the configuration of the integrated computational elements, the inventors discovered that integrated computational elements may be deployed in a small, planar array, with the integrated computational elements being optically coupled to a planar array detector. As used herein, the term "planar array detector" will refer to a photosensitive device having at least two optical detection regions that are laterally spaced apart from one another in an x-y coordinate plane. The optical detection regions are responsive to an input of photons thereon and may also be sensitive to the surrounding temperature conditions, as discussed hereinbelow. More specifically, the inventors discovered that by disposing an integrated computational element on at least one optical detection region of a planar array detector, the integrated computational element may be used to analyze for a characteristic in a manner similar to that of conventional optical computing device configurations. The remaining optical detection regions of the planar array detector may have additional integrated computational elements and/or other optical features associated therewith, which may facilitate the analysis of the same characteristic or one or more different characteristics. In addition, a blank detection region may be present in order to provide a correction factor for thermal variations in the array detector's response. Illustrative array detector configurations are discussed in more detail hereinbelow.

Disposition of one or more integrated computational elements on a planar array detector may provide a number of advantages. Of most significant note, planar array detectors can be very small in size, thereby allowing the array detector and the integrated computational element(s) associated therewith to be maintained in a relatively small operational space compared to that of conventional optical computing device configurations. In addition, the device configurations disclosed herein can provide a considerably shorter optical train compared to conventional device configurations in which the integrated computational element(s) and a detector are laterally spaced apart from one another.

In the illustrative embodiments of the present disclosure, photons within the optical train leading to the planar array detector are distributed between the detector's optical detection regions, thereby lowering the number of photons incident upon each optical detection region. In contrast, conventional optical computing device configurations generally convey a much higher fraction of the incident photons to a detector. Although the decreased number of incident photons might be expected to lower detection sensitivity and increase analytical noise, the inventors discovered that small detector arrays still allow sufficiently accurate analyses to be conducted.

In particular embodiments, the inventors discovered that a 2×2 planar array detector (see FIGS. 3 and 4) can be particularly suitable in this regard, since the four detection regions do not result in excessive distribution of the incident photons. In a 2×2 planar array detector, up to three integrated computational elements and blank detection region may be accommodated thereon, thereby facilitating analyses of up to three different characteristics while providing for correction of thermal variation in the detector. Although a 2×2 planar array detector may be particularly advantageous, it is to be recognized that both larger detector arrays (e.g., a 3×3 array, a 3×2 array, or the like) or smaller detector arrays (e.g., a 2×1 array or a 3×1 array) may be used to accommodate the needs of a particular application. Non-rectangular detector arrays may also be used without department from the scope of the present disclosure. For example, in some embodiments, a hexagonal detector array may be used. Larger detector arrays may be desirable, for example, when more extensive analytical processing capabilities are needed within a target detection region. Moreover, the detection regions within the detector array may also take on any geometric shape, and the square detection regions shown in the drawings should not be considered limiting. For example, in some embodiments, hexagonal detection regions may allow an array with a very high detection density to be realized by close packing the hexagonal detection regions together. Collimating optics may be incorporated within the optical train to direct a sufficient number of incident photons upon the various optical detection regions to improve sensitivity and accuracy.

The inventors also discovered additional optical computing device modifications that are not only complementary to the planar array detectors discussed above, but also facilitate further decreases in operational profile to be realized, in addition to providing other advantages. One such modification involves forming optically transparent sampling windows within the optical train from a castable material that is optically transparent to the electromagnetic radiation present therein. Specifically, the inventors discovered that sampling windows may be fabricated as a multi-level "tiered" structure (see FIGS. 8-11) in which multiple o-ring seals or a similar sealing mechanism around at least a portion of the tiers may provide isolation against the sampling environment. A compression fitting may be used to compact the tiered sampling window structure within its housing to complete the sealing process. The tiered sampling window structure may be more mechanically robust than existing non-tiered sampling window configurations, which are frequently brazed in place, with the brazing being positioned such that it undergoes exposure to a potentially harsh and/or high-temperature/high-pressure sampling environment. The material within the brazing may particularly be susceptible to corrosion under these conditions, thereby leading to premature seal failure. Hence, the tiered sampling window structure disclosed herein may improve structural reliability within the optical train of optical computing devices. With regard to decreasing the operational profile of optical computing devices, the tiered sampling window structure may allow thinner sampling windows to be used. The tiered sampling window structure may also allow coupling optics to be omitted from the "backside" of the sampling window. In addition, at least one surface of the sampling window structure may be fabricated as a lens, which may allow photon collimation to be realized within the optical train without incorporating additional collimating optics, which would otherwise occupy additional space. Casting of the sampling windows may also be advantageous from an ease of fabrication standpoint.

Figure 6:
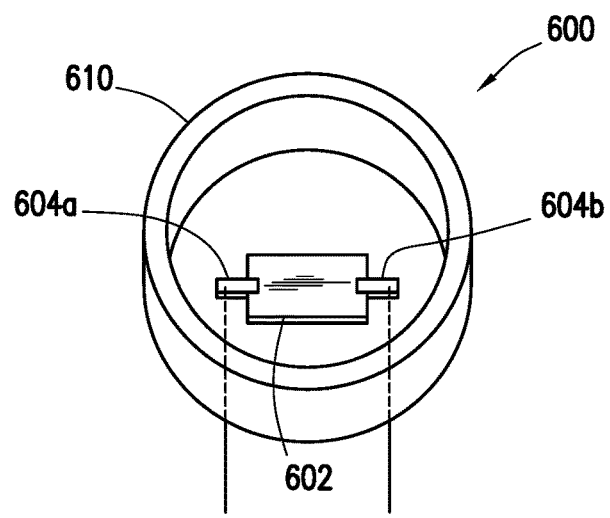
FIG. 6 is a diagram of an illustrative planar, thermal blackbody emitter.

Another beneficial modification for reducing the operational profile of optical computing devices is replacement of the electromagnetic radiation sources conventionally used in conjunction with optical computing devices (e.g., filament-based "point" sources) with a planar, thermal blackbody emitter (see FIG. 6). Planar, thermal blackbody emitters may be resistively heated under low-power conditions to produce a broad wavelength distribution of emitted electromagnetic radiation. Suitable planar, thermal blackbody emitters include, but are not limited to, those available from Intex (Pordenone, Italy), such as exemplary product numbers INTX 22-1000, INTX 17-0900 and INTX 08-0300. These planar, thermal blackbody emitters provide a distribution of emitted wavelengths over a range of about 1-20 microns upon resistive heating, with the predominant emitted wavelengths falling near 3 microns and varying in position to some degree depending upon the actual heating temperature. Not only are planar, thermal blackbody emitters low-power devices, but they are also resistant to thermal and environmental degradation, collectively making them well suited for use downhole and in other harsh sampling environments. Planar, thermal blackbody emitters are also small in size, thereby further facilitating miniaturization of optical computing devices.

Even more advantageously, planar, thermal blackbody emitters are capable of stable pulsed operation up to a frequency of about 150 Hz, which allows the electromagnetic radiation provided within an optical train to be chopped by virtue of the source's operation, rather than by employing a mechanical chopper to improve detection sensitivity. In contrast, filament-based electromagnetic radiation sources are believed to be unsuitable for being stably pulsed in this manner. Hence, use of a planar, thermal blackbody emitter can allow further reductions in operational profile to be realized by allowing a mechanical chopper to be omitted from the optical train.

Because a broad spectrum of wavelengths is produced by planar, thermal blackbody emitters, it may be beneficial to employ optical bandpass filters in conjunction with the planar array detector, thereby allowing only a desired subset of emitted wavelengths to pass to the optical detection regions after optically interacting with any integrated computational elements associated therewith. Even when optical bandpass filters are incorporated in the embodiments disclosed herein, they do not significantly increase the operational profile of the optical computing devices, thereby maintaining the advantages discussed hereinabove. Suitable optical bandpass filters can be identified by one having ordinary skill in the art and can be incorporated within an optical computing device, as discussed hereinbelow.

Characteristics of a sample that may be analyzed according to the present disclosure are not believed to be particularly limited. Illustrative characteristics that may be assayed using integrated computational elements include, for example, analyte concentrations, impurity content, viscosity, density, opacity, color, refractive index, liquid content, oxidation state, particle size, pH, salinity, total dissolved solids, ionic strength, porosity, bacteria content, combinations thereof, and the like.

Optical computing devices may be configured to assay as many characteristics as desired for a given sample. All that is required to assay multiple characteristics is the incorporation of suitable integrated computational elements for measuring each characteristic. When using a planar array detector, a detector array sized to accommodate the desired number of integrated computational elements is used. Since the properties of a sample may be a combination of the properties of the various substances therein, (e.g., a linear, non-linear, logarithmic, and/or exponential combination of the properties), the more characteristics that are assayed, the more accurately the properties of the sample can be determined.

As used herein, the term "electromagnetic radiation" will refer to radio waves, microwave radiation, infrared and near-infrared radiation, visible light, ultraviolet light, X-ray radiation or gamma ray radiation. In more particular embodiments, the electromagnetic radiation may comprise infrared radiation in a wavelength range of about 1,000 nm to about 25,000 nm, or about 1,000 nm to about 20,000 nm, or about 1,000 nm to about 15,000 nm, or about 2,000 nm to about 10,000 nm, or about 2,000 nm to about 5,000 nm. Fluorescent, phosphorescent, or blackbody emissions and/or the like from the sample may also be analyzed using an optical computing device, and in such embodiments, a source of electromagnetic radiation may be omitted.

As used herein, the term "optically interact" and grammatical variations thereof will refer to the reflection, transmission, scattering, diffraction, or absorption of electromagnetic radiation on, through, or from a sample or an integrated computational element. Accordingly, the term "optically interacted electromagnetic radiation" will refer to electromagnetic radiation that has been reflected, transmitted, scattered, diffracted, or absorbed by, emitted, or re-radiated from a sample or an integrated computational element. In the embodiments, of the present disclosure, electromagnetic radiation that has optically interacted with an integrated computational element and reached an optical detection region of a planar array detector comprises transmitted electromagnetic radiation by virtue of their disposition with respect to one another, as discussed hereinafter.

As used herein, the term "sample" or other variants thereof will refer to at least a portion of a substance of interest to be analyzed using an optical computing device. It is to be understood that a sample need not necessarily represent a discrete aliquot of a bulk material. Rather, sampling of a bulk material may take place through a sampling window, wherein the bulk material may be static or flowing during the analysis.

In some embodiments, a sample being analyzed by the optical computing device may comprise a fluid. As used herein, the term "fluid" will refer to any substance that is capable of flowing, including particulate solids, liquids, gases, slurries, emulsions, powders, muds, glasses, any combination thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid. Illustrative gases that can be analyzed according to the present disclosure include, for example, air, nitrogen, carbon dioxide, argon, helium, hydrogen sulfide, mercaptan, thiophene, methane, ethane, butane, and other hydrocarbon gases, combinations thereof and/or the like.

Various downhole treatment operations may be observed by monitoring a treatment fluid or formation fluid using the optical computing devices disclosed herein. Illustrative treatment operations that may be observed include, for example, drilling operations, fracturing operations, gravel packing operations, acidizing operations, scale dissolution and removal operations, consolidation operations, diverting operations, the like, and any combination thereof. The treatment fluid or the formation fluid may be monitored at any point during the treatment operation, including downhole. In further embodiments, feedback obtained from the optical computing device may allow a proactive change to be made in the treatment operation.

In some or other embodiments, the sample being analyzed by the optical computing device may comprise a solid. Solids may include, for example, drill cuttings, wellbore surfaces, and the like.

Figure 2:
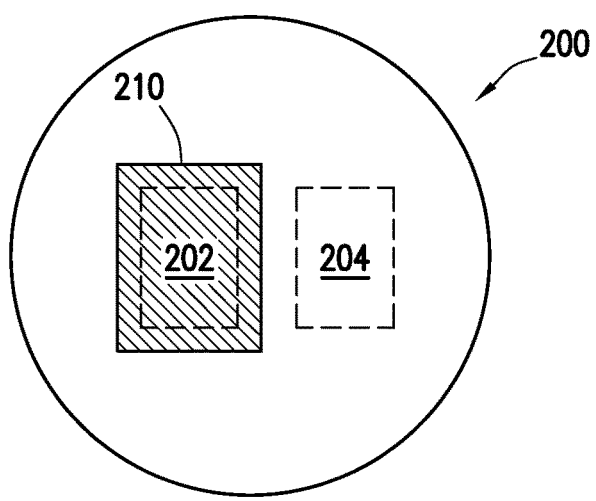
FIGS. 2-4 are diagrams that illustrate exemplary planar array detector configurations having at least one integrated computational element associated therewith.
Figure 3:
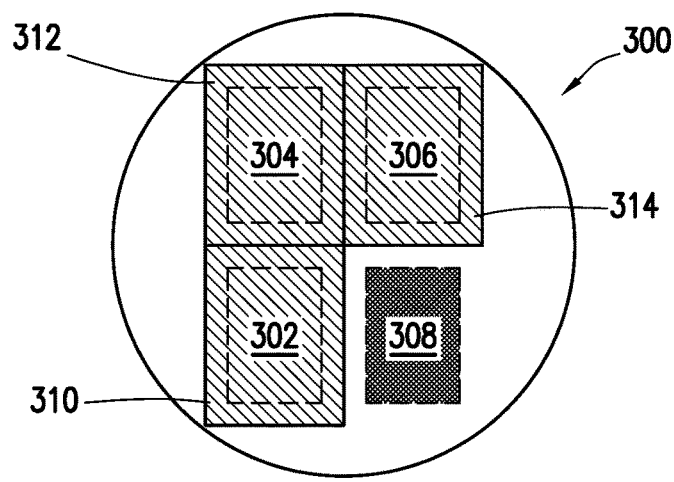
Figure 4:
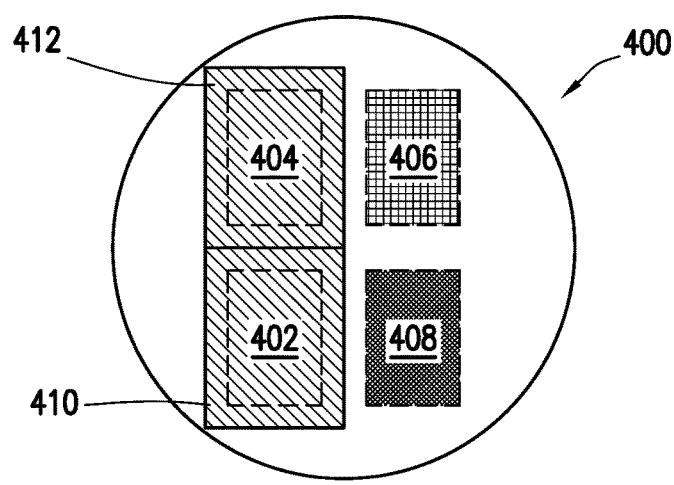

The planar array detectors of the present disclosure will now be described with reference to the drawings. FIGS. 2-4 are diagrams that illustrate exemplary planar array detector configurations having at least one integrated computational element associated therewith. As shown in FIG. 2, planar array detector 200 is a 2×1 array detector having detection regions 202 and 204 present therein. In the configuration depicted in FIG. 2, detection region 202 is an optical detection region that is overlaid with integrated computational element 210, and detection region 204 is either a neutral detection region or a blank detection region. Integrated computational element 210 may overlap the edges of detection region 202, as depicted, or it may match the shape of detection region 202, in some embodiments. As used herein, the term "neutral detection region" will refer to an optical detection region that is configured to receive an input of photons from an optical train but without optically interacting the photons with an integrated computational element. As used herein, the term "blank detection region" will refer to an optical detection region of a planar array detector that is blocked from receiving an input of photons from an optical train in which the array detector is present. Accordingly, any detector response from the blank detection region is primarily due to thermal effects. As discussed in more detail hereinafter, the detector output of a neutral detection region and/or a blank detection region may be used to correct and/or normalize the detector output of an optical detection region that is overlaid with an integrated computational element. Both a neutral detection region and a blank detection region may be present in some embodiments of larger arrays, as discussed in more detail hereinbelow.

In other various embodiments, the detector output of a first optical detection region having an integrated computational element associated therewith may be corrected or normalized by the detector output of a second optical detection region having a different integrated computational element associated therewith. Hence, in such embodiments, a neutral detection region and/or a blank detection region may be unnecessary.

FIGS. 3 and 4 are diagrams that illustrate exemplary 2×2 planar array detector configurations. The 2×2 planar array detectors include at least one blank detection region and integrated computational elements overlaying at least two of the optical detection regions. As discussed above, the response of the blank detection region may be used to correct for thermal variations in the detector output from the optical detection regions associated with the integrated computational elements. In some embodiments, an integrated computational element may overlay the remaining optical detection region, as depicted in FIG. 3. In other embodiments, the remaining optical detection region may comprise a neutral detection region, as depicted in FIG. 4. FIGS. 3 and 4 are described in more detail hereinafter.

FIG. 3 shows array detector 300 configured as a 2×2 planar array detector having detection regions 302, 304, 306 and 308. In the configuration depicted in FIG. 3, detection regions 302, 304 and 306 comprise optical detection regions that are overlaid, respectively, with integrated computational elements 310, 312 and 314. Detection region 308 comprises a blank detection region.

Likewise, FIG. 4 shows array detector 400 configured as a 2×2 planar array detector having detection regions 402, 404, 406 and 408. In the configuration depicted in FIG. 4, detection regions 402 and 404 comprise optical detection regions that are overlaid, respectively, with integrated computational elements 410 and 412. Detection region 406 is also an optical detection region comprising a neutral detection region and does not have an integrated computational element associated therewith. However, other optical constructs, such as bandpass filters and the like, may be located in the optical train leading to detection region 406, as discussed hereinafter. Detection region 408 comprises a blank detection region.

When the planar array detector has two or more integrated computational elements associated therewith, the integrated computational elements may be each associated with a characteristic of interest, each disassociated with a characteristic of interest or any combination thereof. Integrated computational elements that are "associated" with a characteristic of interest substantially mimic the regression vector related with that characteristic. In contrast, integrated computational elements that are "diassociated" with a characteristic of interest do not substantially mimic the regression vector related to that characteristic. Accordingly, associated integrated computational elements may be predictive of a characteristic of interest by themselves, whereas disassociated integrated computational elements are not predictive by themselves. However, as alluded to above, the outputs of two or more different integrated computational elements (e.g., all associated, all disassociated, or a combination of associated and disassociated) may be physically or computationally combined to be predictive of a characteristic of interest. Physical combinations can include optically interacting electromagnetic radiation with multiple integrated computational elements in sequence. Computational combinations can include obtaining a detector output related to each integrated computational element and then applying a ratio or other mathematical function of the two detector outputs to determine a characteristic of interest. The physical or computational combination of the integrated computational elements may be more predictive of the characteristic of interest than are the individual integrated computational elements alone.

Accordingly, when two or more integrated computational elements are associated with a planar array detector, the integrated computational elements may be used to analyze collectively for a single characteristic or individually for different characteristics. When analyzing collectively for a single characteristic, the detector outputs may be computationally combined, as generally discussed above, optionally with a further temperature correction factor applied from the blank detection region.

For example, in array detector 400 of FIG. 4, the detector outputs of detection regions 402 and 404 may be computationally combined to determine a single characteristic, or the detector outputs of detection regions 402 and 404 may each be corrected with the neutral detector output of detection region 406 to determine separate characteristics. When analyzing for separate characteristics, integrated computational elements 410 and 412 are each generally associated with the characteristics of interest. A further temperature correction factor may be applied from the output of blank detection region 408, as discussed above.

In order to restrict the wavelengths of electromagnetic radiation passing to the planar array detector, a bandpass filter may be present in the optical train leading to each detection region. That is, a bandpass filter may overlay each detection region, including both those that do and do not have an integrated computational element associated therewith. Optionally, the bandpass filter may overlay the blank detection region, although other means for restricting the blank detection region from receiving electromagnetic radiation from the optical train may be present. In some embodiments, separate bandpass filters may overlay each optical detection region. The separate bandpass filters associated overlaying each optical detection region may be the same or different. Different bandpass filters may be used when it is desired to expose the various optical detection regions to differing wavelengths of electromagnetic radiation. In other various embodiments, a monolithic bandpass filter may collectively overlay each optical detection region and optionally the blank detection region. In either case, bandpass filters suitable for transmitting a desired wavelength range may be readily identified by one having ordinary skill in the art.

Figure 5:
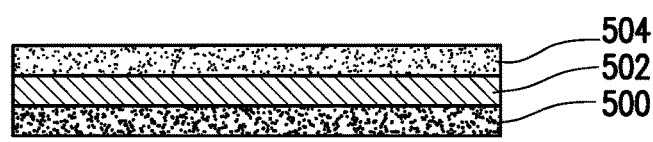
FIG. 5 is a diagram that illustrates a side view of a single optical detection region having an integrated computational element and a bandpass filter disposed thereon.

In the interest of clarity, bandpass filters are not depicted in FIGS. 2-4 discussed above. Generally, the bandpass filters overlay the optical detection region by being stacked upon the integrated computational element, if present, such that the integrated computational element is disposed between the optical detection region and the bandpass filter. FIG. 5 is a diagram that illustrates a side view of a single optical detection region 500 having an integrated computational element 502 and a bandpass filter 504 disposed thereon. When a bandpass filter overlays a neutral detection region (not shown), the bandpass filter may be disposed directly upon the optical detection region.

Integrated computational elements may be introduced to a planar array detector in several different fashions, any of which may allow a reduction in operating space to be realized. In some embodiments, an integrated computational element may be directly grown upon an optical detection region of a planar array detector by a suitable thin film deposition process. In other various embodiments, an integrated computational element may be grown separately from the planar array detector, and the integrated computational element may be harvested as a wafer of an appropriate size and placed upon the optical detection region. In still other embodiments, an integrated computational element may be grown upon a surface of a bandpass filter using a suitable thin film deposition process. Thereafter, the combined bandpass filter and integrated computational element may be transferred to the planar array detector such that the integrated computational element is sandwiched between the bandpass filter and the optical detection region, as depicted in FIG. 5.

Accordingly, in various embodiments, optical analysis tools containing optical computing devices comprising a planar array detector are described herein. Various other components of the optical analysis tools are described hereinbelow.

In various embodiments, the optical analysis tools can comprise: an electromagnetic radiation source that provides electromagnetic radiation to an optical train; and an optical computing device positioned within the optical train, the optical computing device comprising a planar array detector having at least two optical detection regions, at least one of the at least two optical detection regions having an integrated computational element disposed thereon. The planar array detector and the integrated computational element are in a fixed configuration with respect to one another. That is, no moving parts are associated with conveying electromagnetic radiation to the various detection regions. The electromagnetic radiation received by the optical detection region associated with the integrated computational element comprises transmitted electromagnetic radiation.

The electromagnetic radiation source may be any device capable of emitting or generating electromagnetic radiation, as defined herein. In illustrative embodiments, the electromagnetic radiation source may comprise a light bulb or other filament-based source, a light emitting device (LED), a laser, a blackbody, a photonic crystal, an X-Ray source, a gamma ray source, any combination thereof, and the like.

In other various and more desirable embodiments, the electromagnetic radiation source may comprise a planar, thermal blackbody emitter, such as the illustrative emitters described hereinabove. As described above, planar, thermal blackbody emitters can also promote miniaturization of an optical computing device due to their small size and favorable geometry compared to filament-type electromagnetic radiation sources. Although planar, thermal blackbody emitters may be particularly beneficial when used in combination with a planar array detector, such emitters may also be used as an electromagnetic radiation source in conventional optical computing devices as well.

FIG. 6 is a diagram of an illustrative planar, thermal blackbody emitter. As depicted in FIG. 6, emitter 600 includes emitting surface 602, to which are attached electrical leads 604a and 604b. Emitting surface 602 may comprise an emitting crystal in some embodiments. Optionally, emitting surface 602 and electrical leads 604a and 604b may be disposed within housing 610 from which electrical leads 604a and 604b extend. In further embodiments (not shown), an elliptical reflector may be disposed within housing 610 to optimize collimation of the exiting electromagnetic radiation and/or a bandpass filter or lens may be defined in a cover on housing 610. As discussed above, such planar, thermal blackbody emitters are capable of stable pulsed operation, thereby allowing a mechanical chopper to be omitted from the optical train of the optical analysis tools described herein.

In order to direct a sufficient number of photons to each optical detection surface, collimating optics may be present within the optical train between the electromagnetic radiation source and the planar array detector. The collimating optics may be present at any location along the optical train, and some suitable locations are described above. In other various embodiments, discussed hereinbelow, collimating optics may also be incorporated within sampling windows of the presently described optical analysis tools. Suitable collimating optics for use within the optical train of the present optical analysis tools will be familiar to one having ordinary skill in the art and may include mirrors and various types of lenses (e.g., convex lenses, Fresnel lenses, and combinations thereof).

Figure 7:
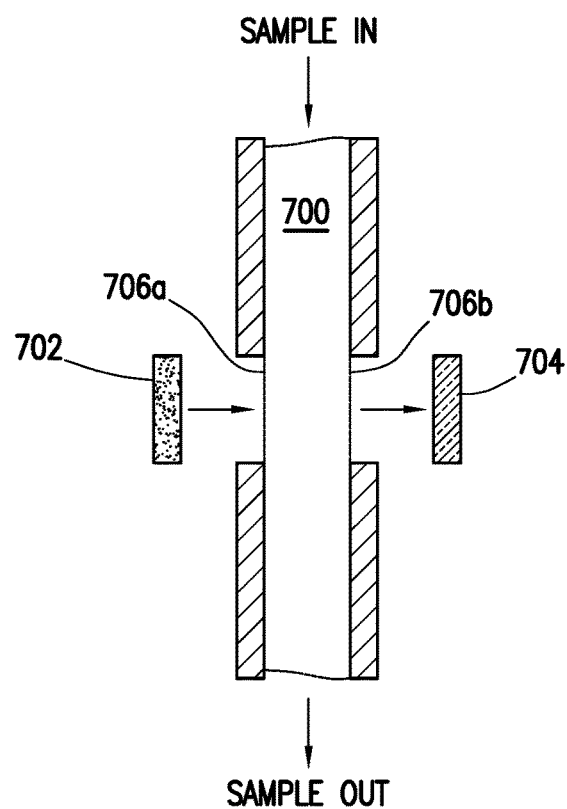
FIG. 7 is a diagram of an illustrative optical analysis tool having a flow pathway defined therein.

The optical analysis tools of the present disclosure also include sampling windows disposed within the optical train, such that the sampling windows define at least a portion of a flow pathway for a sample. FIG. 7 is a diagram of an illustrative optical analysis tool having a flow pathway defined therein. As shown in FIG. 7, flow pathway 700 is located between electromagnetic radiation source 702 and detector 704, where sampling windows 706a and 706b are defined along flow pathway 700 and allow electromagnetic radiation to travel from electromagnetic radiation source 702 to detector 704.

Referring still to FIG. 7, in more specific embodiments, electromagnetic radiation source 702 may comprise a planar, thermal blackbody emitter and may be understood more completely by reference to FIG. 6. Similarly, in more specific embodiments, detector 704 may comprise a planar array detector having at least one integrated computational element disposed thereon and may be understood more completely by reference to FIGS. 2-5. It should be recognized, however, that the detector configurations of FIGS. 2-5 are for purposes of illustration and should not be considered limiting of the configurations that may be present. Related optical components such as bandpass filters and collimating optics, for example, have not been depicted in FIG. 7 in the interest of clarity.

In more particular embodiments, sampling windows 706a and 706b defined along flow path 700 may be formed from a castable material that is substantially transparent to electromagnetic radiation that is present within the optical train. As discussed above, by forming optically transparent sampling windows through a casting technique, a robust and compact sampling window structure may be obtained. In addition, in some embodiments, at least one surface of the sampling windows may be structured as a lens for collimating the electromagnetic radiation within the optical train. In more specific embodiments, the castable transparent material may comprise castable sapphire, which is commercially available from Surmet Corporation (Burlington, Mass.) under the tradename ALON.

Figure 8:
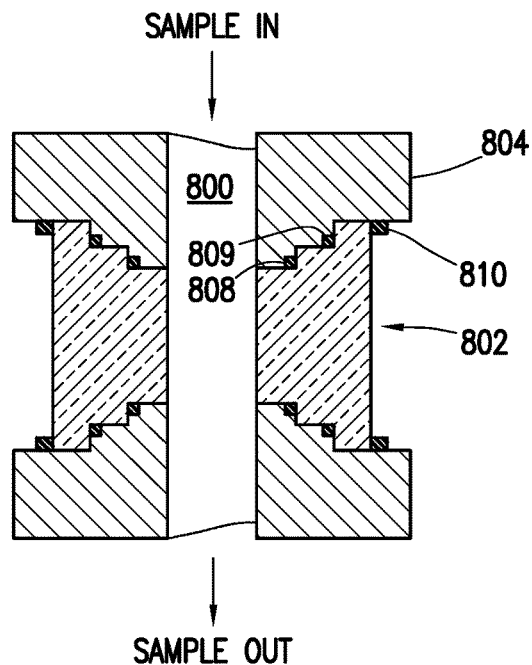
FIGS. 8 and 9 are diagrams that show tiered sampling windows defining a portion of a flow pathway for a sample.
Figure 9:
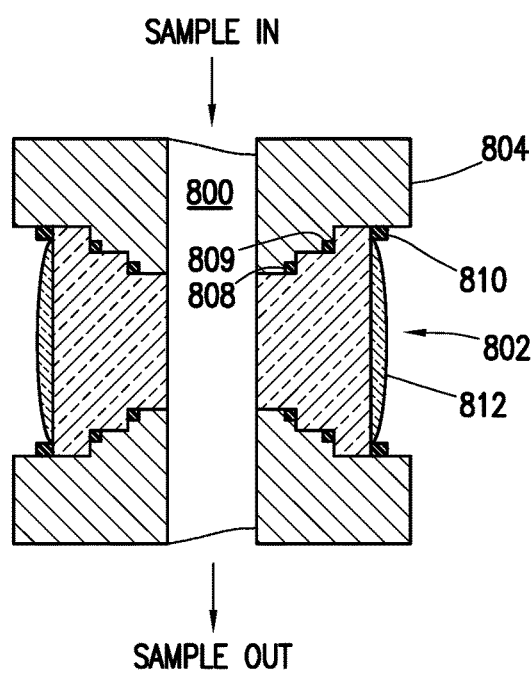

In more specific embodiments, the optical analysis tools of the present disclosure may comprise a tiered sampling window, such as those depicted in FIGS. 8 and 9. FIGS. 8 and 9 are diagrams that show tiered sampling window structures defining a portion of a flow pathway for a sample. For example, the flow pathway may comprise a flow line, a pipeline, a wellbore, an annulus defined within a wellbore, or any flow lines or pipelines extending to or from a wellbore. Referring to FIGS. 8 and 9, flow pathway 800 is defined, in part, by sampling window 802. Sampling window 802 is affixed within housing 804, which defines at least a portion of the remainder of flow pathway 800. Sampling window 802 is tiered and its levels become progressively longer with respect to the longitudinal axis of flow pathway 800 upon proceeding outwardly therefrom, reasons for which will be discussed hereinafter. In some embodiments, sampling window 802 may be monolithic. Although FIGS. 8 and 9 have depicted sampling window 802 as having three tiers, it may have as few as two tiers. Alternately, more tiers may be present, if desired.

Sampling window 802 is sealed from flow pathway 800 by one or more o-rings or a similar sealing mechanism. As depicted in FIGS. 8 and 9, a seal is created around a first tier by o-ring 808, and a seal is created around a second tier by o-ring 809. In the configuration of FIGS. 8 and 9, o-ring 809 serves as a backup seal for o-ring 808 in the event of incomplete sealing. The multiple seals within sampling window 802 are facilitated by its tiered structure, which may be advantageous over a conventional cylindrical window assembly under high operating pressures. If a backup o-ring seal is deemed unnecessary, a two-tiered sampling window may be present, as discussed above. Similarly, if additional sealing capabilities are needed, further tiers and accompanying o-rings may be present. Other operational considerations may dictate the number of tiers needed for a particular situation, such as, for example, the sample pressure within flow pathway 800 and/or the overall thickness of sampling window 802.

Referring still to FIGS. 8 and 9, sampling window 802 is held in place by a compression fitting, such as by retaining ring 810. Retaining ring 810 compresses o-rings 808 and 809 against housing 804 and facilitates their sealing functionality.

In still further embodiments, at least one surface of sampling window 802 may be structured as a lens for collimating electromagnetic radiation within the optical train. As shown in FIG. 9, lens 812 is disposed on the outerward-facing surface of sampling window 802. Lens 812 may be fabricated separately (e.g., by casting) and then be adhered to the outward-facing surface of sampling window 802. Alternately, lens 810 may be defined on the outward-facing surface of sampling window 802 during its fabrication such that a monolithic sampling window structure is maintained. Any suitable lens structure (e.g., convex, concave, Fresnel and the like) may comprise lens 812 upon sampling window 802.

Figure 10:
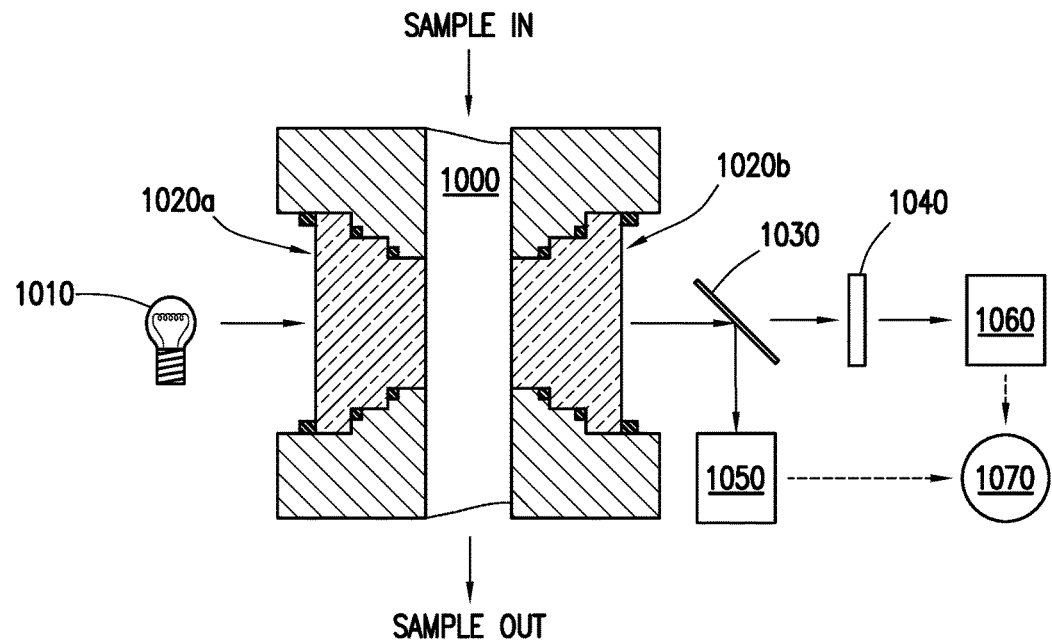
FIG. 10 is a diagram that illustrates a conventional optical computing device configuration in which electromagnetic radiation is transmitted through tiered sample windows.

Although FIGS. 8 and 9 have depicted tiered sampling windows that may be particularly advantageous when used in conjunction with the optical analysis tools of the present disclosure, it is to be recognized that they may also be used in conjunction with more conventional configurations for optical computing devices, if desired. For example, FIG. 10 is a diagram that illustrates a conventional optical computing device configuration in which electromagnetic radiation is transmitted through a tiered sampling window. As depicted in FIG. 10, source 1010 provides electromagnetic radiation to a sample present within flow pathway 1000 after traversing tiered sampling window 1020a. Subsequently, electromagnetic radiation exits flow pathway 1000 via tiered sampling window 1020b and encounters beam splitter 1030. A portion of the electromagnetic radiation is directed to integrated computational element 1040, and a portion of the electromagnetic radiation is directed to detector 1050. The electromagnetic radiation directed to detector 1050 does not encounter integrated computational element 1040, and the output of detector 1050 may be used to account for deviations within the optical train (e.g., radiating deviations in source 1010 or optically opaque buildup on sampling windows 1020a or 1020b). That is, the electromagnetic radiation detected by detector 1050 corresponds to the detector output of the neutral optical element, discussed above. The portion of the electromagnetic radiation directed to integrated computational element 1040 optically interacts therewith and undergoes a change that is representative of the sample characteristic being measured. The optically interacted electromagnetic radiation leaving integrated computational element 1040 then encounters detector 1060 and produces a signal that is proportional to the amount of electromagnetic radiation received and the magnitude of the characteristic. The output of detector 1060 may then be corrected with the output of detector 1050 in signal processing unit 1070. Various other optical components, such as a chopper, may be disposed in the optical train of the configuration of FIG. 10, but are not shown in the interest of clarity.

In an alternative configuration (also not shown), integrated computational element 1040 may be replaced with a movable array of integrated computational elements, wherein different integrated computational elements may become disposed in the optical train at various points in time. For example, the movable array of integrated computational elements may comprise a rotatable array in which different integrated computational elements are exposed to electromagnetic radiation by turning the array. Alternatively, the movable array may comprise a reciprocating array, in which the array is moved laterally back and forth as a function of time in order to expose different integrated computational elements to electromagnetic radiation within the optical train. When a movable array of integrated computational elements is employed, beam splitter 1030 and detector 1050 may be omitted, since a blank position in the movable array (i.e., a position not housing an integrated computational element) may be used to account for variations within the optical train.

Accordingly, in various embodiments, the present disclosure provides optical analysis tools comprising one or more of a planar, thermal blackbody emitter, a flow pathway containing a tiered sampling window and a planar array detector (e.g., a 2×2 planar array detector).

In more specific embodiments, all three of the foregoing components may be present. Such optical analysis tools may comprise an electromagnetic radiation source comprising a planar, thermal blackbody emitter that provides electromagnetic radiation to an optical train; an optical computing device positioned within the optical train that comprises a 2×2 planar array detector having at least two optical detection regions and at least one of the at least two optical detection regions having an integrated computational element disposed thereon; wherein the 2×2 planar array detector and the integrated computational element are in a fixed configuration with respect to one another; and tiered sampling windows within the optical train that define a portion of a flow pathway for a sample, the tiered being sealed from the flow pathway and comprising a substance that is substantially transparent to electromagnetic radiation within the optical train. In some embodiments, the tiered sampling windows may comprise three tiers, with the tiered sampling windows being sealed by a first o-ring and a second o-ring and being held in place via a compression fitting.

Figure 11:
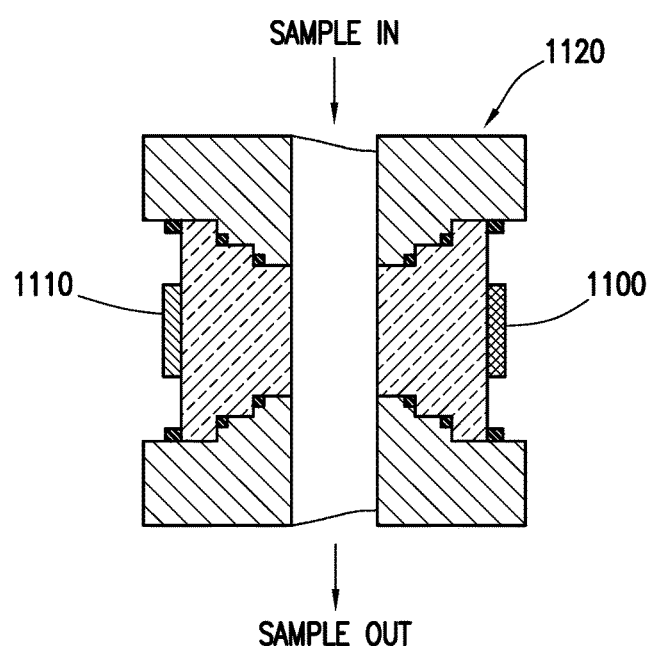
FIG. 11 is a diagram of an illustrative optical analysis tool in which a planar, thermal blackbody emitter, a flow pathway containing tiered sampling windows, and a planar array detector are used in combination with one another.

FIG. 11 is a diagram of an illustrative optical analysis tool in which a planar, thermal blackbody emitter, a flow pathway containing tiered sampling windows, and a planar array detector are used in combination with one another. Planar array detector 1100 may have a structure similar to that depicted in FIGS. 2-4 and may be better understood by reference thereto. Likewise, planar, thermal blackbody emitter 1110 may have a structure similar to that depicted in FIG. 6 and flow pathway/sampling window 1120 may have a structure similar to that depicted in FIGS. 8 and 9. As depicted in FIG. 11, planar array detector 1100 and planar, thermal blackbody emitter 1110 may be placed upon the outerward-facing surface of the sampling windows within flow pathway/sampling window 1120. Such configurations keep space utilization to a minimum. In other configurations, planar array detector 1100 and/or planar, thermal blackbody emitter 1110 may be laterally spaced apart from the sampling windows of flow pathway/sampling window 1120.

In still other various embodiments, a planar, thermal blackbody emitter may be used as the electromagnetic radiation source in combination with a conventional optical computing device. Accordingly, such optical analysis tools may comprise: an electromagnetic radiation source that provides electromagnetic radiation to an optical train, the electromagnetic radiation source comprising a planar, thermal blackbody emitter; and an optical computing device positioned within the optical train, the optical computing device comprising at least one integrated computational element, and a detector that receives electromagnetic radiation that has optically interacted with the at least one integrated computational element. The optical computing device may have a configuration similar to that described above in reference to FIG. 10.

In still other various embodiments, a tiered sampling window may be present in combination with a conventional optical computing device. Accordingly, such optical analysis tools may comprise: an electromagnetic radiation source that provides electromagnetic radiation to an optical train; an optical computing device positioned within the optical train, the optical computing device comprising at least one integrated computational element, and a detector that receives electromagnetic radiation that has optically interacted with the at least one integrated computational element; and tiered sampling windows within the optical train that define a portion of a flow pathway for a sample, the tiered sampling windows being sealed from the flow pathway and comprising a substance that is substantially transparent to electromagnetic radiation within the optical train. The optical computing device may have a configuration similar to that described above in reference to FIG. 10. In some embodiments, the tiered sampling windows may comprise three tiers, with the tiered sampling windows being sealed by a first o-ring and a second o-ring and being held in place via a compression fitting.

It is to be recognized that various embodiments herein may operate under computer control and may include various blocks, modules, elements, components, methods, and algorithms that may be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable programmable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Given the description above, it is to be recognized that the optical computing devices of the present disclosure may be used for determining various characteristics of a sample, particularly a fluid. In various embodiments, such methods may comprise: optically interacting electromagnetic radiation with a sample and a planar array detector having at least two optical detection regions, at least one of the at least two optical detection regions having an integrated computational element disposed thereon; and generating an output signal from the detector corresponding to a characteristic of the sample. In some embodiments, the planar array detector may comprise multiple integrated computational elements, and the output of the integrated computational elements may be computationally combined with one another in determining the characteristic of the sample.

In some embodiments, the sample may comprise a fluid. In some embodiments, the methods may comprise flowing the fluid between a source of electromagnetic radiation and the planar array detector. The fluid may flow in a flow pathway having tiered sampling windows, such as tiered sampling windows formed from castable sapphire.

In some or other embodiments, the source of electromagnetic radiation may comprise a planar, thermal blackbody emitter. In further embodiments, methods for determining a characteristic of the sample may comprise pulsing the planar, thermal blackbody emitter. As discussed above, pulsing the source of electromagnetic radiation in this manner may function as a non-mechanical means of chopping the electromagnetic radiation.

In more specific embodiments, the optical computing devices of the present disclosure may be used in conjunction with a subterranean treatment operation by monitoring a treatment fluid, a formation fluid, or any combination thereof. Illustrative treatment fluids and treatment operations in which the optical computing devices of the present disclosure may be used are described hereinabove.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site.

Embodiments herein include:

A. Optical analysis tools comprising a planar array detector. The optical analysis tools comprise: an electromagnetic radiation source that provides electromagnetic radiation to an optical train; and an optical computing device positioned within the optical train, the optical computing device comprising a planar array detector having at least two optical detection regions, at least one of the at least two optical detection regions having an integrated computational element disposed thereon; wherein the planar array detector and the integrated computational element are in a fixed configuration with respect to one another.

B. Optical analysis tools comprising a 2×2 planar array detector, a planar, thermal blackbody emitter and tiered sampling windows. The optical analysis tools comprise: an electromagnetic radiation source that provides electromagnetic radiation to an optical train, the electromagnetic radiation source comprising a planar, thermal blackbody emitter; an optical computing device positioned within the optical train, the optical computing device comprising a 2×2 planar array detector having at least two optical detection regions, at least one of the at least two optical detection regions having an integrated computational element disposed thereon; wherein the 2×2 planar array detector and the integrated computational element are in a fixed configuration with respect to one another; and tiered sampling windows within the optical train that define a portion of a flow pathway for a sample, the tiered sampling windows being sealed from the flow pathway and comprising a substance that is substantially transparent to electromagnetic radiation within the optical train.

C. Optical analysis tools comprising a planar, thermal blackbody emitter and an optical computing device comprising an integrated computational element. The optical analysis tools comprise: an electromagnetic radiation source that provides electromagnetic radiation to an optical train, the electromagnetic radiation source comprising a planar, thermal blackbody emitter; and an optical computing device positioned within the optical train, the optical computing device comprising at least one integrated computational element, and a detector that receives electromagnetic radiation that has optically interacted with the at least one integrated computational element.

D. Optical analysis tools comprising tiered sampling windows and an optical computing device comprising an integrated computational element. The optical analysis tools comprise: an electromagnetic radiation source that provides electromagnetic radiation to an optical train; an optical computing device positioned within the optical train, the optical computing device comprising at least one integrated computational element, and a detector that receives electromagnetic radiation that has optically interacted with the at least one integrated computational element; and tiered sampling windows within the optical train that define a portion of a flow pathway for a sample, the tiered sampling windows being sealed from the flow pathway and comprising a substance that is substantially transparent to electromagnetic radiation within the optical train.

E. Methods for analyzing a characteristic of a sample. The methods comprise: optically interacting electromagnetic radiation with a sample and a planar array detector having at least two optical detection regions, at least one of the at least two optical detection regions having an integrated computational element disposed thereon; and generating an output signal from the detector corresponding to a characteristic of the sample.

Each of embodiments A-E may have one or more of the following additional elements in any combination:

Element 1: wherein the planar array detector further comprises a blank detection region that is blocked from receiving electromagnetic radiation from the optical train.

Element 2: wherein at least one of the at least two optical detection regions comprises a neutral detection region.

Element 3: wherein the planar array detector comprises a 2×2 planar array detector.

Element 4: wherein the planar array detector comprises three optical detection regions and the blank detection region.

Element 5: wherein each of the optical detection regions have an integrated computational element disposed thereon.

Element 6: wherein two of the optical detection regions have an integrated computational element disposed thereon and one of the optical detection regions comprises a neutral detection region.

Element 7: wherein a bandpass filter overlays each optical detection region.

Element 8: wherein separate bandpass filters overlay each optical detection region.

Element 9: wherein a monolithic bandpass filter collectively overlays each optical detection region.

Element 10: wherein the integrated computational element is directly deposited on an optical detection region of the planar array detector.

Element 11: wherein the electromagnetic radiation source comprises a planar, thermal blackbody emitter.

Element 12: wherein the electromagnetic radiation source is capable of pulsed operation.

Element 13: wherein the optical analysis tool further comprises: collimating optics within the optical train between the electromagnetic radiation source and the planar array detector.

Element 14: wherein the optical analysis tool further comprises: tiered sampling windows within the optical train that define a portion of a flow pathway for a sample, the tiered sampling windows being sealed from the flow pathway and comprising a substance that is substantially transparent to electromagnetic radiation within the optical train.

Element 15: wherein the tiered sampling windows comprise three tiers, the tiered sampling windows being sealed with a first o-ring and a second o-ring and being held in place via a compression fitting.

Element 16: wherein at least one surface of the tiered sampling windows is structured as a lens for collimating the electromagnetic radiation within the optical train.

Element 17: wherein the tiered sampling windows are formed from castable sapphire.

Element 18: wherein the 2×2 planar array detector further comprises a blank detection region that is blocked from receiving electromagnetic radiation from the optical train.

Element 19: wherein the 2×2 planar array detector comprises three optical detection regions and the blank detection region.

Element 20: wherein the integrated computational element is directly deposited on an optical detection region of the 2×2 planar array detector.

Element 21: wherein the sample comprises a treatment fluid or a formation fluid.

Element 22: wherein the planar array detector comprises at least two optical detection regions with an integrated computational element disposed thereon, a neutral detection region, and a blank detection region that is blocked from receiving electromagnetic radiation.

Element 23: wherein the method further comprises computationally combining an output from the at least two optical detection regions having an integrated computational element disposed thereon.

By way of non-limiting example, exemplary combinations applicable to A include the optical analysis tool of A in combination with: elements 1 and 2; elements 1 and 3; elements 1-3; elements 1-4; elements 1, 3, and 5; elements 1, 3, and 6; elements 1, 3, and 7; elements 1, 3, 7 and 8; elements 1, 3, 7 and 9; elements 1-3 and 7; elements 1-3 and 10; elements 1-3 and 11; elements 11 and 13; elements 1-3 and 14; elements 11, 14, and 15; elements 1-3, 14, and 16; and, elements 11, 14, and 17.

By way of non-limiting example, exemplary combinations applicable to B include the optical analysis tool of B in combination with: elements 15 and 17; elements 15 and 18; elements 15 and 19; elements 18 and 19; elements 18, 19, and 20; elements 7, 18, and 19; elements 15 and 16; elements 6 and 19; and, elements 15 and 16.

By way of non-limiting example, exemplary combinations applicable to C include the optical analysis tool of C in combination with: elements 13 and 14 and elements 12 and 13.

By way of non-limiting example, exemplary combinations applicable to D include the optical analysis tool of D in combination with: elements 13 and 15; elements 13 and 16; and, elements 15 and 17.

By way of non-limiting example, exemplary combinations applicable to E include the optical analysis tool of E in combination with: elements 21 and 22; elements 22 and 23; and, elements 1 and 2.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. An optical analysis tool comprising:
an electromagnetic radiation source that provides electromagnetic radiation to an optical train; and
an optical computing device positioned within the optical train, the optical computing device comprising a planar array detector having at least two optical detection regions, at least one of the at least two optical detection regions having an integrated computational element disposed thereon;
wherein the planar array detector and the integrated computational element are in a fixed configuration with respect to one another.

2. The optical analysis tool of claim 1, wherein the planar array detector further comprises a blank detection region that is blocked from receiving electromagnetic radiation from the optical train.

3. The optical analysis tool of claim 2, wherein at least one of the at least two optical detection regions comprises a neutral detection region.

4. The optical analysis tool of claim 2, wherein the planar array detector comprises a 2×2 planar array detector.

5. The optical analysis tool of claim 4, wherein the planar array detector comprises three optical detection regions and the blank detection region.

6. The optical analysis tool of claim 5, wherein each of the optical detection regions have an integrated computational element disposed thereon.

7. The optical analysis tool of claim 5, wherein two of the optical detection regions have an integrated computational element disposed thereon and one of the optical detection regions comprises a neutral detection region.

8. The optical analysis tool of claim 5, wherein a bandpass filter overlays each optical detection region.

9. The optical analysis tool of claim 1, wherein a bandpass filter overlays each optical detection region.

10. The optical analysis tool of claim 1, wherein the electromagnetic radiation source comprises a planar, thermal blackbody emitter.

11. The optical analysis tool of claim 10, further comprising:
collimating optics within the optical train between the electromagnetic radiation source and the planar array detector.

12. The optical analysis tool of claim 1, further comprising:
tiered sampling windows within the optical train that define a portion of a flow pathway for a sample, the tiered sampling windows being sealed from the flow pathway and comprising a substance that is substantially transparent to electromagnetic radiation within the optical train.

13. The optical analysis tool of claim 12, wherein at least one surface of the tiered sampling windows is structured as a lens for collimating the electromagnetic radiation within the optical train.

14. An optical analysis tool comprising:
an electromagnetic radiation source that provides electromagnetic radiation to an optical train, the electromagnetic radiation source comprising a planar, thermal blackbody emitter;
an optical computing device positioned within the optical train, the optical computing device comprising a 2×2 planar array detector having at least two optical detection regions, at least one of the at least two optical detection regions having an integrated computational element disposed thereon;
wherein the 2×2 planar array detector and the integrated computational element are in a fixed configuration with respect to one another; and
tiered sampling windows within the optical train that define a portion of a flow pathway for a sample, the tiered sampling windows being sealed from the flow pathway and comprising a substance that is substantially transparent to electromagnetic radiation within the optical train.

15. The optical analysis tool of claim 14, wherein the 2×2 planar array detector further comprises a blank detection region that is blocked from receiving electromagnetic radiation from the optical train.

16. The optical analysis tool of claim 15, wherein at least one of the at least two optical detection regions comprises a neutral detection region.

17. The optical analysis tool of claim 15, wherein the 2×2 planar array detector comprises three optical detection regions and the blank detection region.

18. The optical analysis tool of claim 17, wherein each of the optical detection regions has an integrated computational element disposed thereon.

19. The optical analysis tool of claim 17, wherein two of the optical detection regions have an integrated computational element disposed thereon and one of the optical detection regions comprises a neutral detection region.

20. The optical analysis tool of claim 14, wherein a bandpass filter overlays each optical detection region.

21. The optical analysis tool of claim 14, wherein at least one surface of the tiered sampling windows is structured as a lens for collimating the electromagnetic radiation within the optical train.

22. An optical analysis tool comprising:
- an electromagnetic radiation source that provides electromagnetic radiation to an optical train;
- an optical computing device positioned within the optical train, the optical computing device comprising at least one integrated computational element, and a detector that receives electromagnetic radiation that has optically interacted with the at least one integrated computational element; and
- tiered sampling windows within the optical train that define a portion of a flow pathway for a sample, the tiered sampling windows being sealed from the flow pathway and comprising a substance that is substantially transparent to electromagnetic radiation within the optical train.

* * * * *